United States Patent
Bertholet et al.

(10) Patent No.: US 8,470,044 B2
(45) Date of Patent: Jun. 25, 2013

(54) INTERVERTEBRAL PROSTHETIC DEVICE

(76) Inventors: Maurice Bertholet, Le Luc (FR);
Francois Vittini, Ollioules (FR)

( * ) Notice: Subject to any disclaimer, the term of this patent is extended or adjusted under 35 U.S.C. 154(b) by 58 days.

(21) Appl. No.: 12/990,827

(22) PCT Filed: May 5, 2008

(86) PCT No.: PCT/FR2008/000631
§ 371 (c)(1),
(2), (4) Date: Nov. 3, 2010

(87) PCT Pub. No.: WO2009/136009
PCT Pub. Date: Nov. 12, 2009

(65) Prior Publication Data
US 2011/0060415 A1    Mar. 10, 2011

(51) Int. Cl.
*A61F 2/44* (2006.01)
(52) U.S. Cl.
USPC .................................................. 623/17.16
(58) Field of Classification Search
USPC ............... 623/17.11–17.16; 606/246–249
See application file for complete search history.

(56) References Cited

U.S. PATENT DOCUMENTS

| 6,579,321 B1 * | 6/2003 | Gordon et al. ............. 623/17.16 |
| 6,595,998 B2 * | 7/2003 | Johnson et al. ................. 606/90 |
| 6,827,743 B2 * | 12/2004 | Eisermann et al. ........ 623/23.54 |
| 2004/0111161 A1 * | 6/2004 | Trieu ......................... 623/17.16 |
| 2005/0085909 A1 | 4/2005 | Eisermann |
| 2005/0165485 A1 * | 7/2005 | Trieu ......................... 623/17.13 |
| 2006/0217715 A1 * | 9/2006 | Serhan et al. ................... 606/61 |
| 2008/0161928 A1 * | 7/2008 | Trieu ......................... 623/17.16 |

FOREIGN PATENT DOCUMENTS

FR    2908291 A1    5/2008

* cited by examiner

*Primary Examiner* — Mary Hoffman
(74) *Attorney, Agent, or Firm* — Bachman & LaPointe, P.C.

(57) ABSTRACT

An intervertebral prosthetic device has a medullary protection shield with a concave shape designed to be adapted to the anatomy of a medullary canal against which the medullary protection shield is able to be positioned, a spherical tough core inside a flexible integral assembly designed for an intervertebral space, and the flexible integral assembly has a truncated parallelepiped shape, wherein a front portion of the truncated parallelepiped shape is higher than a rear portion of the truncated parallelepiped shape, and wherein the rear portion is concave and corresponds to the concave shaped medullary protection shield.

8 Claims, 2 Drawing Sheets

INTERVERTEBRAL PROSTHETIC DEVICE

BACKGROUND

The present invention relates generally to a biocompatible, implantable intervertebral device for spinal surgery, with a tough inner part for force distribution and medullary canal protection within a flexible elastomer block, reinforced at the upper and lower ends thereof by a yoke coated with a bone osteoconductive material and provided with an attachment member.

This spinal surgery, and more specifically in the cervical condition in question, is subject to degenerative or accidental phenomena affecting the osteodiscal junctions of the cervical column. Prior procedures made use of total intervertebral disk excision with or without replacement of said disk by a bone graft or substitutes such as coral or cervical cages. These various techniques resulted in definitive stiffening of the two adjacent vertebral segments. This gave rise to the idea of implanting a prosthesis made of biocompatible materials in order to prevent cervical stiffening resulting in long-term over- or underlying disk damage and provide the cervical column with the all the movements permitted. A number of parts intended to be implanted between two vertebrae to remedy intervertebral constituent tissue degeneration or wear are known. All these parts have the common feature of needing to retain spacing between two vertebrae. Such parts are hereinafter referred to as "implantable parts".

More specifically, forming a type of elastic polymer intercalation pad completely covered with a tissue is known (U.S. Pat. No. 3,867,728).

Moreover, a further model (WO9900074) using an elastic polymer also relates to complete covering with a tissue, with extensions used for attaching the implant.

SUMMARY OF THE INVENTION

These coverings of the entirety of "implantable parts" with tissue have the drawback of being in direct contact with the bone element of the vertebrae and the lateral or longitudinal movements exerted at this point may induce a friction effect, the short and long-term effects of which in terms of friction-related inflammatory reaction and in terms of particle release with subsequent expulsion of tissue fragments against bone marrow and radices are not foreseeable.

Similarly, said "implantable parts", due to the integral elastic elastomer composition thereof, do not account for the fact that the pressures exerted thereon are not distributed evenly whereas, physiologically, they are different, hence the benefit of a "hard spot" as described which centralizes and enhances the distribution of the forces applied.

In the preferred embodiment, the aim of the present invention (FIG. 1) consists of including, inside a biocompatible integral assembly (1) generally made of silicone, a device (FIG. 2) characterized in that it comprises a rigid portion consisting of two adjoining parts: a "shield" (2) and a ball (3). The whole is optionally connected by a connection part but always so as to form an integral assembly.

DETAILED DESCRIPTION OF THE PREFERRED EMBODIMENT(S)

Figure 2:
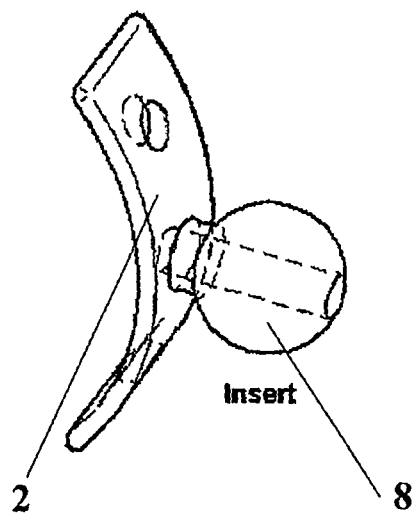
FIG. 2—Representation of the entire internal part with the protective shield (2) and the adjoining ball (8) for force distribution.

The part, known as a "shield" (2) necessarily made of rigid material, has a concave shape (FIG. 2) designed to observe the anatomy of the medullary canal against which it is to be positioned. This shield (2) has a protective role during compression or excessive movements, such that there is no silicone creep against the medullary canal under the effect of pressure, liable to give rise to medullary complications due to bone marrow compression and radicular complications due to compression of the radices. It serves as the posterior vertebral ligament generally excised during the surgical procedure and frequently damaged under certain conditions.

Figure 3:
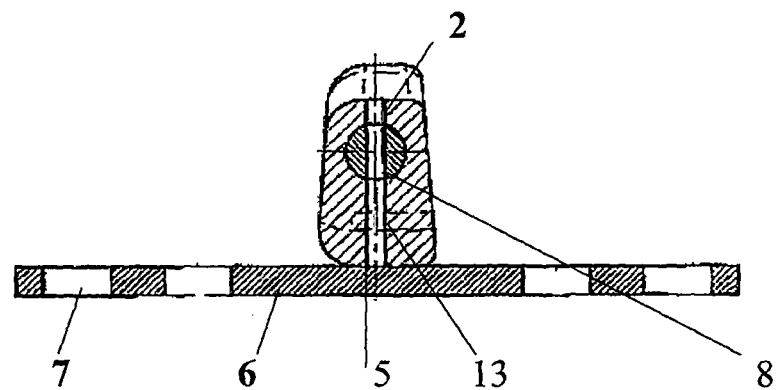
FIG. 3—Profile view of the entire implant with specifically the shield (2), the ball (8), the attachment plate (6) with the holes (7) thereof and one of the orifices (13 or 5) provided for the barium sulfate markers.

The ball (8) or central core optionally connected to the "shield" (FIG. 2) by a connection member, but always adjoining said shield, is the equivalent of the normal nucleus. It would ideally be positioned in the first third (FIG. 3) of the concave portion (9) of the silicone part so as to be the central axis through which the pressure, rotation, bearing, movement forces pass, thus enabling the centralization and homogeneous radial distribution of these forces inside the implant. Without it, these forces would be applied anarchically on the entire prosthesis and would favor the damage thereof. The presence thereof would thus make it possible to prevent internal deformations followed potentially by elastomer separations. This perfectly spherical ball (8) is made of a tough biocompatible material suitable for withstanding the continuous high pressures exerted thereon.

To ensure satisfactory cohesion of the ball and the shield, both members will be connected by a connection member which may be a portion of an integral assembly made of one part or the joining by means of assembly, bonding or any other means of the "portions" ("shield", ball, connection member) of the internal assembly.

This internal assembly is thus included in a biocompatible integral part (1), ideally made of flexible material, but sufficiently suitable for undergoing lateral, longitudinal or axial rotation movements, while in compression. Also, in view of existing products and accounting for the need for this biocompatibility, a medical grade silicone corresponding to the physiological pressure values was selected, it being understood that any products having the features described above may also be suitable.

Figure 1:
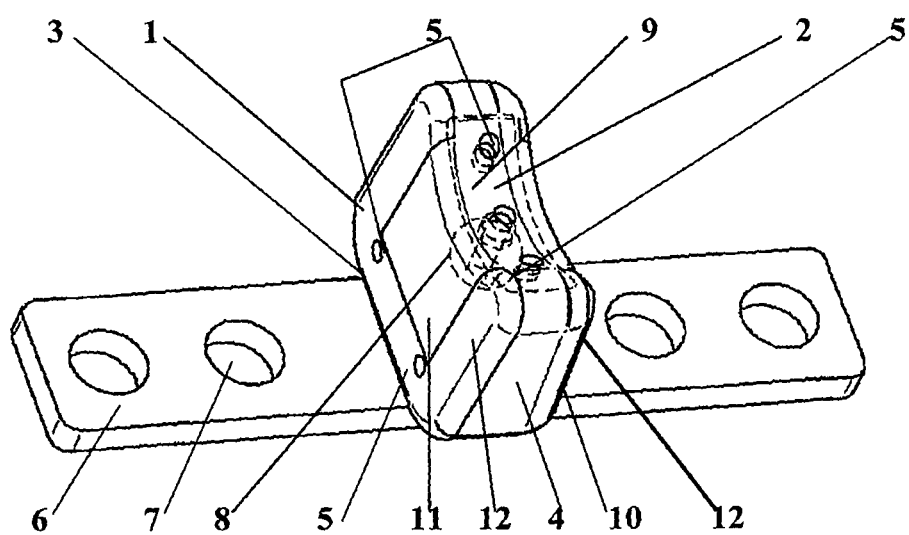
FIG. 1—General view of the implant showing the entire implantable part.

This silicone integral member has a truncated parallelepipedic shape (1) since the front portion (3) thereof adjoining the attachment plate (6) is higher than the concave rear portion thereof (FIG. 3), in order to observe the morphology of the implantation site. However, it is also above all to observe the natural overall curvature of the spinal column overall. The radius of the concave portion (9) has also been designed to observe the anatomy of the medullary canal against which it is to be positioned. This integral implant would have rounded angles on the entire periphery thereof. The upper (11) and lower (10) surfaces are reinforced by a yoke-shaped part (12) (FIG. 1). This yoke molded in a biocompatible material, such as silicone, has a higher hardness than the central parallelepiped. It is applied on the over- and underlying vertebral plates between which it is compressed. The pressure forces reverberated on the central part enable same to fill the entire cavity evenly. Finally, these yokes are also used for pressure force distribution in lateral and flexion movements of the cervical spine and may prevent premature wear of the central parallelepiped. To adapt the implant to each subject's morphology, three basic types of different dimensions and thickness are devised, but always observing a parallelepipedic shape.

Figure 4:
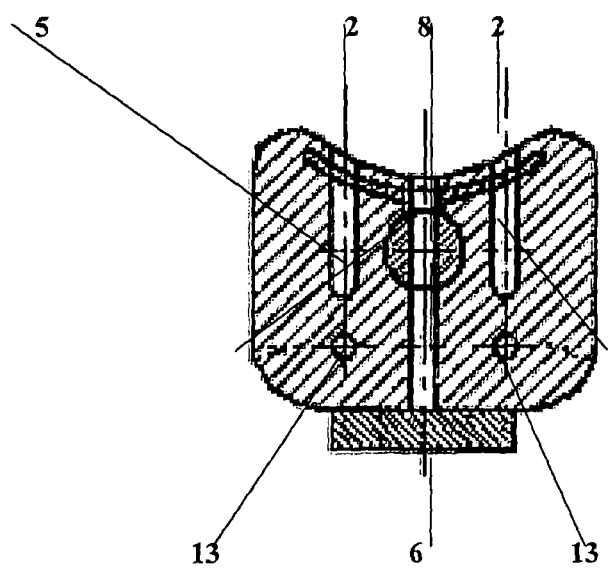
FIG. 4—Top view of the part with the ball (8) adjoining the shield (2), the horizontal (5) and vertical (13) barium sulfate markers and the attachment plate (6).

On the posterior portion of the truncated parallelepiped, thus in the thinnest portion thereof, adjoining the concave portion (9), two vertical orifices (5) (FIG. 4), one in each angle. X-ray markers used for locating the implanted part are included in both orifices. These markers are ideally an inclusion of polymer charged with barium sulfate. The latter product, which is biocompatible, is preferred to metallic markers such as gold or titanium wires so as to prevent any risk of exclusion of these metallic members in adjacent tissues. The positioning of these markers makes it possible to situate the implant with respect to the spinal canal and in relation to the bone marrow. Similarly, however, in this instance, to enable the easy marking of the implant in relation to the pressure axis, two further markers (13), horizontal in this case (FIG. 4), would depart from the corners of the anterior base towards the two posterior ends.

To ensure, during excessive movements or compression, that excessively high silicone pressure does not occur due to a creep effect against the medullary canal liable to cause medullary complications due to compression of the bone marrow and radicular complications due to compression of the radix, a rigid part (2) characterized in that it is integral via a connection part with the ball (8) has been inserted and provides protection against any untimely overflow. It serves as the as the posterior vertebral ligament generally excised during the surgical procedure and frequently damaged under certain conditions. This part (2) also ideally made of a tough biocompatible material has a similar radius of curvature to the concavity of said concave posterior end (9). It is noted that the ball and the rigid concave part may be integral and made of two parts which are subsequently joined to form a rigid assembly.

The ball (8) or central core equivalent to the normal nucleus would ideally be positioned in the first third of the concave portion (9) of the silicone part so as to be the central axis through which the pressure, rotation, bearing, movement forces pass, thus enabling the centralization and homogeneous radial distribution of these forces inside the implant. Without it, these forces would be applied anarchically on the entire prosthesis and would favor the damage thereof. The presence thereof would thus make it possible to prevent internal deformations followed potentially by elastomer separations. This perfectly round ball (8) is made of a tough biocompatible material suitable for withstanding the continuous high pressures exerted thereon.

The outer periphery (4) of the part (1) is encircled by a strip of tissue characterized in that it is open-worked. Ideally made of polyester, it is applied on the periphery thereof to polymerize the polymer so that it is perfectly adherent to the constituent material of the implant, or that this material still in the pasty phase literally includes said tissue by the material overflows during polymerization creeping through the meshes. Once polymerization is complete, the tissue becomes a constituent part of the periphery of the implant and prevents, when the device is implanted, any untimely creep thereof under the effect of potentially higher pressures than those envisaged.

The entire part is treated by ion implantation which improves the surface features thereof. There is thus a reduction in the friction coefficient and reduction in the risk of adhesive wear liable to cause particle release. This ion implantation is long-term.

On the upper (11) and lower (10) faces (FIG. 1) of the parallelepipedic implant, osteoconductive or osteoinductive products such as hydroxyapatite or any other similar osteogenesis vector product are deposited. In the case of hydroxyapatite, the product, like any product in powder or grain form, is also included either before the end of polymerization or using a bonding agent, but partially. In both cases, this procedures a solid attachment of said powder or grains but enables the adjoining tissues to be in direct contact with these osteoconductive or osteoinductive agents, generating satisfactory implant integration.

The front portion includes an attachment plate (6) with holes (7) (FIG. 1) for inserting screws rigidly connecting said attachment plate to the upper vertebra and to the lower vertebra of the implantation site. This attachment plate (6) adjoining the implant is made of the same material as the implant. It is reinforced on the inside by a strip of tissue ideally made of open-worked polyester. This type of tissue adds to the flexibility of the polymer, an excellent strength which, combined with the natural elasticity of said product, enables it to be subject to stress without deformation by the various spinal movements. Moreover, the number of holes is not limitative since it is possible to increase the number thereof. Similarly, the surgeon may only retain one of each side by cutting said attachment plate. Moreover, the existence of two holes (7) on either side of the implant enables, in the event of double implantation, the rigid connection of two parts using a single screw.

This type of implant described in this instance more for use in the cervical spine may equally well be used in dorsolumbar disk conditions provided that the implant dimensions are suitable for the dimensions of the vertebral parts and/or the parallelepipedic formulation is replaced by a cylindrical formulation while retaining the other features mentioned above.

The invention is not limited to the embodiments described herein, but the invention is extended to all the imaginable alternative embodiments remaining within the spirit and the general scope of the invention.

The invention claimed is:

1. Intervertebral prosthetic device comprising a medullary protection shield with a concave shape designed to be adapted to the anatomy of a medullary canal against which the medullary protection shield is able to be positioned, a spherical tough core inside a flexible integral assembly designed for an intervertebral space, and the flexible integral assembly has a truncated parallelepiped shape, wherein a front portion of the truncated parallelepiped shape is higher than a rear portion of the truncated parallelepiped shape, wherein the rear portion is concave and corresponds to the concave shaped medullary protection shield, and wherein the medullary protection shield extends from the spherical tough core.

2. Intervertebral prosthetic device according to claim 1, wherein the flexible integral assembly comprises upper and lower surfaces having a periphery which is reinforced by a stronger yoke.

3. Intervertebral prosthetic device according to claim 1, wherein the device is ion-treated to reinforce surface features thereof.

4. Intervertebral prosthetic device according to claim 2, further comprising said device being covered with an osteogenic agent on the upper and lower surfaces adapted to be in contact with the lower and upper vertebrae.

5. Intervertebral prosthetic device according to claim 1, further comprising on a vertical periphery of the device in relation to an insertion in a spinal column, a surface inclusion of an open-worked reinforcing polyester tissue.

6. Intervertebral prosthetic device according to claim 1, further including in a posterior portion thereof in relation to a spinal column, an attachment plate with holes, the attachment plate being made of flexible polymer reinforced internally with an extensible open-worked tissue.

7. Intervertebral prosthetic device according to claim 1, further comprising X-ray marking means via orifices filled with barium sulfate.

8. Intervertebral prosthetic device according to claim 1, further having dimensions suitable for use in at least one of cervical situations and lumbar situations.

\* \* \* \* \*